United States Patent [19]

Egerer et al.

[11] Patent Number: 4,857,461
[45] Date of Patent: Aug. 15, 1989

[54] CONTINUOUS PROCESS FOR THE ENZYMATIC PREPARATION OF ISOMALTULOSE

[75] Inventors: Peter Egerer, Kirchseeon; Wulf Crueger, Erkrath; Günter Schmidt-Kastner, Wuppertal, all of Fed. Rep. of Germany

[73] Assignee: Bayer Aktiengesellschaft, Leverkusen, Fed. Rep. of Germany

[21] Appl. No.: 855,222

[22] Filed: Apr. 23, 1986

[30] Foreign Application Priority Data

Apr. 27, 1985 [DE] Fed. Rep. of Germany ....... 3515284
Aug. 10, 1985 [DE] Fed. Rep. of Germany ....... 3528752

[51] Int. Cl.⁴ ............................................. C12P 19/24
[52] U.S. Cl. ...................................... 435/94; 435/97; 435/100; 435/174; 435/177; 435/178; 435/179; 435/180; 435/181; 435/182; 435/800; 435/813; 435/815; 435/819; 435/847; 435/880
[58] Field of Search ................. 435/94, 97, 100, 174, 435/177, 178, 179, 180, 181, 182, 847, 880, 800, 813, 819, 815

[56] References Cited

U.S. PATENT DOCUMENTS

| | | | |
|---|---|---|---|
| 4,359,531 | 11/1982 | Bucke et al. ........................ | 435/97 |
| 4,390,627 | 6/1983 | Lantero ............................... | 435/177 |
| 4,525,457 | 6/1985 | Sakata et al. ...................... | 435/180 |
| 4,663,163 | 5/1987 | Hou et al. .......................... | 435/179 |

FOREIGN PATENT DOCUMENTS

| | | |
|---|---|---|
| 0001099 | 3/1979 | European Pat. Off. . |
| 0028900 | 5/1981 | European Pat. Off. . |
| 0049801 | 4/1982 | European Pat. Off. . |
| 1049800 | 1/1959 | Fed. Rep. of Germany . |
| 3038219 | 4/1982 | Fed. Rep. of Germany . |
| 3038218 | 5/1982 | Fed. Rep. of Germany . |
| 2179966 | 11/1973 | France . |

OTHER PUBLICATIONS

Cheethan, P. S. J., "Principles of Industrial Enzymology: Basis of Utilization of Soluble and Immobilized Enzymes in Industrial Processes", in: Wiseman, A., *Handbook of Enzyme Biotechnology*, (Chichester, England, 1985), Ellis Horwood Ltd., 2nd ed., pp. 79–86.

S. Schmidt-Berg-Lorenz, W. Mauch, Z Zuckerindustrie 14, 625–627 (1964).

Technische Rundschau, Band 77, Nr. 38, 17. Sep. 1985, Seiten 38,39,42,43,Bern, CH; U. Beerstecher: "Forschung und Innovation auf der Achema 1985", *Figur 1*.

*Primary Examiner*—Robert A. Wax
*Attorney, Agent, or Firm*—Sprung Horn Kramer & Woods

[57] ABSTRACT

The present invention relates to a continuous process for the enzymatic preparation of isomaltulose. A periplasmatic sucrose-mutase is produced by fermentation of microorganisms which form sucrose-mutase. The cell-free crude enzyme extract is prepared by digestion of the cells and by cross-flow microfiltration. In a single-stage, simultaneous purification and immobilization of the sucrose-mutase from the cell-free crude extract conditioned by diafiltration is obtained by selective bonding to an anionizable carrier matrix. Direct conversion of sucrose into isomaltulose is produced by the sucrose-mutase bonded to the anionizable carrier matrix, preferably in cartridge or cartouche form.

13 Claims, 4 Drawing Sheets

CONTINUOUS PROCESS FOR THE ENZYMATIC PREPARATION OF ISOMALTULOSE

A continuous process has been found for the enzymatic preparation of isomaltulose in a reactor system operated under sterile conditions, which is characterized in that, in a reactor system which can be operated under sterile conditions,
(a) sucrose-mutase is prepared by fermentation of microorganisms which form sucrose-mutase, the cells already being treated with salt solution and surface-active reagents before the end of the logarithmic growth phase,
(b) a cell-free crude enzyme extract is prepared in a manner which is known per se by cell digestion and cross-flow microfiltration,
(c) the sucrose-mutase from this crude extract is simultaneously purified and immobilized by selective bonding to an anionizable carrier matrix and
(d) the matrix thereby obtained is brought into contact with sucrose.

According to German Patent Specification No. 1,049,800, sucrose is converted into isomaltulose by enzymes of microbial origin. In addition to *Protaminobacter rubrum*, other bacteria, such as *Erwinia carotovora, Serratia marcescens, Serratia plymuthica* and *Leuconostoc mesenteroides*, are capable of this biotransformation [S. Schmidt-Berg-Lorenz, W. Mauch, Z. Zuckerindustrie 14, 625–627 (1964); F. H. Stodola, 126th Meeting Amer. Chem. Soc. September 1954, Abstr. of Papers S. D 5; W. Mauch, S. Schmidt-Berg-Lorenz, Z. Zuckerindustrie 14, 309–315 and 375 383 (1964)].

On this basis, various processes have been described for microbial or enzymatic preparation of isomaltulose.

European Patent Specification No. 1,009, for example, describes a process for the continuous fermentation of microorganisms with simultaneous conversion of sucrose to isomaltulose. U.S. Pat. No. 4,386,158, DE-OS (German Published Specification) No. 3,038,219 and European Patent Specification No. 28,900 describe various processes for the preparation of isomaltulose with immbolized microorganisms.

In DE-OS (German Published Specification) No. 3,038,218, for the first time, the enzyme sucrose-mutase is described and characterized and its immobilization and use for the preparation of isomaltulose are recorded.

The isolation of the enzyme sucrose-mutase is thereby described as batchwise in a multi-stage process and the subsequent immobilization is described as a separate reaction step. In particular, the chromatography on CM-Sephadex C-50 thereby used is time-consuming. The fermentation steps, the cell digestion, the enzyme purification and the immobilization of the purified enzyme are then carried out in a tedious series of process steps which, in addition, can be carried out under germ-free conditions only with difficulty.

The methods so far described are non-sterile processes for the preparation of isomaltulose by immobilized microorganisms or by immobilized sucrose-mutase, which in addition can be carried out only batchwise from the fermentation to the end product isomaltulose.

In contrast, the process according to the invention is a continuous process, in a reactor system operated under sterile conditions, for the enzymatic preparation of isomaltulose, consisting of the production of periplasmatic sucrose-mutase by fermentation of microorganisms which form sucrose-mutase, preparation of the cell-free crude enzyme extract by digestion of the cells and by cross-flow microfiltration, single-stage, simultaneous purification and immobilization of the sucrose-mutase from the cell-free crude extract conditioned by diafiltration by selective bonding to an anionizable carrier matrix, and direct conversion of sucrose into isomaltulose by the sucrose-mutase bonded to the corresponding anionizable carrier matrix, preferably in cartridge or cartouche form.

In particular, the use of a sulfonic acid cation exchanger in the form of a web matrix makes the exceptionally selective bonding of the sucrose-mutase from the crude enzyme extract possible at very high flow rates and thereby leads to purification of the enzyme in one step. For use of the sucrose-mutase as a biocatalyst for conversion of sucrose into isomaltulose, the enzyme no longer has to be eluted from the cation exchanger and concentrated. The anionizable carrier matrix, in particular a sulfonic acid cation exchanger, bonds the sucrose-mutase so firmly that operation also as a bioreactor is possible over a prolonged period without loss in activity (Example 1).

The use of a sulfonic acid matrix in cartridge or cartouche form, such as is available, for example, from AMF, Molecular Separations Division, Merident, CT, USA in the various commercial forms Zetaprep 100-SP ® or Zetaprep 3000-SP ®, is particularly advantageous. This is crosslinked cellulose containing sulfonic acid, processed to sheets of paper and wound in cartridge form.

Anionic sterile filter cartridges from various manufacturers, for example Ultipor GF ® filter medium from Pall, can be used in a similar manner. In this case, a glass fibre material is enclosed by a resin with highly negatively charged functional groups.

In comparison with the AMF Zetaprep-SP ® system series, which has been brought onto the market for chromatographic purposes, the commercially available sterile filter cartridges are, however, folded membranes or webs, the stream of substrate passing through only one layer of membrane or web. In a cylindrically wound web or membrane sheet, the characteristic of a preferred variant of the process according to the invention, the stream of substrate must, in contrast, pass through many web or membrane layers radially to the cylinder axis.

The high flow rates which are possible in the selective isolation of the sucrose-mutase from the crude extract are likewise advantageous for subsequent operation of the reactor with high percent strength sucrose solution. This is one of the preconditions for high productivity of the sucrose-mutase bioreactor.

Combination of the fermentation step, the cell digestion, the single-stage, simultaneous working-up and immobilization process and the biotransformation step accordingly allows a continuous overall process for enzymatic preparation of isomaltulose which can be operated under germ-free conditions in a very simple manner (FIGS. 1a, b).

An overall process operated under sterile conditions for the enzymatic preparation of isomaltulose which is realized particularly advantageously by the process steps according to the invention prevents entry of germs into the bioreactor and hence the formation of by-products from the substrate sucrose. Such by-products are usually organic acids, microbial metabolism products which can lead to a reduction in the pH value in the bioreactor and hence to inactivation of the sucrose-mutase.

The sucrose-mutase loses its catalytic activity in an extremely short time at temperatures greater than +40° C., so that autoclaving is eliminated as the sterilisation method. The use of most bactericides or fungicides for germ destruction would require very expensive product purification and related analysis because of the use of the product isomaltulose as a sugar substitute.

It is particularly advantageous if the cation exchanger matrix has a high concentration of sulfonic acid functional groups. According to Example 1, it has been possible to bond more than 1 g of pure sucrose-mutase onto one AMF Zeptaprep 100-SP ® unit. According to the specification of the manufacturer, for example, the capacity of the Zetaprep 100-DEAE ® unit is 4–6 g of bovine serum albumin [AMF Inc., LC.10.10, 30.11.1984]. The upper limit of the capacity for sucrose-mutase is accordingly probably likewise about 4 g per Zetaprep 100-SP ®.

About 30 reactor volumes/hour are quoted as the maximum flow rates for chromatography of protein-containing aqueous solutions for the product AMF Zetaprep ® [AMF Inc., LC.10.1G, 28.9.1983].

According to Example 1, 7 reactor volumes per hour were achieved on throughput of a 50% strength sucrose solution with the aid of a peristaltic pump customary in the laboratory. If pumps of greater capacity are used, for example the cog wheel pumps frequently used in the sugar industry, an increased delivery is possible for utilization of higher enzyme loadings.

Generally, for a catalytic reaction, it is of considerable importance for the reactor volume to be kept as small as possible, thus, for example, the fixed bed volume of an immobilized biocatalyst in particle form. This requires a biocatalyst of high activity per unit volume or of high loading density or activity density.

It is thereby possible to carry out the production in smaller reactor units and hence to save considerable plant, energy and maintenance costs.

On the basis of the process according to the invention, product streams of 5–10 reactor volumes/hour can be achieved for the conversion of sucrose into isomaltulose when 50% strength sucrose solution is employed (Example 1). In comparison, product streams which are possible with immobilized cells are of the order of 0.5–1.0 reactor volumes/hour.

The process according to the invention therefore also comprises the use of a radial type bioreactor for biotransformation reactions. As FIGS. 2a and b show, the substrate stream is passed through the various windings of the cellulose web in the cylindrical reactor vessel radially to the cylinder axis towards the discharge, an area gradient per winding and hence a residence time gradient over the entire web surface being present on passage through the cellulose web.

The rate of passage through the cellulose web increases from the outermost to the innermost winding; at the same time the web surface per winding decreases. When enzymes are charged uniformly, there is decrease in the amount of enzymes per winding towards the innermost winding. The residence time of the material stream is thus lower for a high conversion, that is to say at a high product concentration and low substrate concentration, than for a low conversion, that is to say for a low product concentration and high substrate concentration. This reduces the by-product formation of enzymatic origin, such as is observed in the rearrangement, catalysed by sucrose-mutase, of sucrose to isomaltulose with the aid of the glucose, fructose, 1,1'-disaccharide and oligosaccharides formed.

As can be seen from Example 1, if sucrose conversion is complete, the concentration of glucose (about 1.0%) and fructose (about 2.0%) is lower than in comparison batches with sucrose-mutase otherwise immobilized (compare DE-OS (German Published Specification) No. 3,038,218), this being another advantage of the process according to the invention.

The process according to the invention is also characterized in particular, in that treatment with NaCl, KCl or other salts, by themselves or in combination with surface-active compounds, such as Tween, Span or Brij, is sufficient to isolate the enzyme from the bacterial cells (preparation of the crude enzyme extract).

However, for the yield in the preparation of the crude enzyme extract, the age of the fermentation is decisive.

As Table 1 shows, the ratio of sucrose-mutase in the cell-free supernatant after treatment with salt and Tween to the total activity of the cell suspension decreases with the age of the cell culture. There is therefore a decisive relationship between the quality of the cell digestion, the enzyme yield and the course of the fermentation.

TABLE 1

Cell digestion of *Protaminobacter rubrum*

Yield of sucrose-mutase in the cell-free supernatant (crude enzyme extract) after digestion with salt solution and surface-active reagents as a function of the fermentation time.
Reference parameter: volume activity of the fermentation solution (units/ml) = 100%.

| Fermentation time | Volume activity of the fermentation solution | Sucrose-mutase in the cell-free supernatant after digestion (%) |
|---|---|---|
| 2 hours | 0.7 units/ml | 31% |
| 4 hours | 1.4 units/ml | 102% |
| 6 hours | 5.6 units/ml | 72% |
| 8 hours | 14.4 units/ml | 79% |
| 10 hours | 14.8 units/ml | 55% |
| 12 hours | 13.1 units/ml | 30% |

The process according to the invention is also characterized in particular, in that selective bonding of the sucrose-mutase from the crude extract is effected in the pH range of 4–12, preferably between pH 5 and 9, at salt concentrations of less than 0.2M, preferably at 1 μM–10 mM. The crude enzyme extract is therefore advantageously first brought to the corresponding salt concentration by diafiltration and conditioned for the single-stage purification and biotransformation. Selective bonding to sulfonic acid cation exchanger matrices can also be carried out in the presence of a high percent strength sucrose solution, for example 40–60% strength.

The process according to the invention is not restricted to sucrose-mutase which is bonded purely ionically or adsorptively to a sulfonic acid matrix. Rather, it may be advantageous for the sucrose-mutase bonded selectively from the crude enzyme extract to be stabilized on the sulfonic acid matrix by treatment with crosslinking agents, such as, for example, by polyfunctional aldehydes, for example glutaraldehyde, or by hexamethylenediamine/carbodiimide.

The process according to the invention is also characterized, in particular, in that the enzyme sucrose-mutase required for the reaction is formed by microorganisms, above all by *Protaminobacter rubrum* [DSM (Deutsche Sammlung von Mikroorganismen (German Collection of Microorganisms)) 2414], *Erwinia carotovora* (ATTC 25206) and *Serratia plymuthica* (ATTC 15928). After inoculation of the microorganisms (0.1–10.0% of inoculum material) onto a nutrient solution containing carbohydrate, nitrogen and inorganic salts and incubation under optimum conditions, the fermentation is interrupted here before the end of the logarithmic phase. The nutrient solutions consist, for example, of thin liquor/thick liquor or/and thin liquor/clarification mixture from a sugar factory with a dry matter content of 1–25%, preferably 2–7%.

It has furthermore been found that the optimum yield of the sucrose-mutase is achieved if the cells are already treated with salt solution and surface-active reagents before the end of the logarithmic growth phase. Fermentation batches which have already undergone transition to the stationary phase or aged fermentation broths exhibit less advantaeous digestion properties in respect of sucrose-mutase: the ratio of the sucrose-mutase activity in the cell-free supernatant after treatment with salt solution and surface-active reagents to the total activity in the non-digested cells decreases drastically (Table 1).

FIGS. 1 *a, b* show flow charts of the overall process according to the invention. It is possible for the fermentation solution to be either digested directly or first concentrated, for example in a ratio of 1:10, by cross-flow microfiltration and for the cell digestion then to be carried out with a reduced cell suspension volume. Cross-flow microfiltration can be carried out, for example, using the product series from Membrana or Millipore. Diafiltration was carried out on the laboratory scale with the aid of the Amicon ultrafiltration unit, membrane PM 10000, or on the pilot scale with the DDS system, membrane exclusion atr molecular weight 6000.

The reactor arrangement shown in FIG. 1*b* for continuous enzymatic preparation of isomaltulose comprises the fermenter unit, the cross-flow microfiltration unit, the diafiltration unit and the bioreactor, which is employed for simultaneous, single-stage purification and immobilization of the sucrose-mutase and for subsequent biotransformation of sucrose into isomaltulose.

In FIG. 1*b*, the reactors are not shown to scale in relation to one another. The volumes of the various units depend on the requirements of the isomaltulose production: throughput of sucrose, productivity of the bioreactor and production amount of isomaltulose required.

Summarizing, the continuous process according to the invention for enzymatic preparation of isomaltulose has the following advantages in comparison with the processes previously disclosed:
 continuous operation of the process from the fermentation to the product isomaltulose is possible;
 sterile operation of the overall process is considerably favoured;
 simultaneous step of purification and immobilization of sucrose-mutase by selective bonding to carboxylate, sulfate, phosphate or other anionic carrier materials, particularly advantageously to a sulfonic acid matrix;
 anionic exchanger matrix in web form, in particular a crosslinked cellulose web, containing sulfonic acid, in cartridge form, wound as a radial type bioreactor, allows high flow rates;
 sucrose-mutase bonded in this manner can be employed directly for the biotransformation sucrose-isomaltulose;
 radial type reactor has the effect of reducing the concentration of the secondary components on the basis of the enzyme activity gradient towards the reactor outlet.

EXAMPLE 1

From a subculture of the strain *Protaminobacter rubrum* Z 12 [DMS (Deutsche Sammlung von Mikroorganismen (German Collection of Microorganisms)) 2414], cells are suspended with 10 ml of a sterile mixture of one part of thick liquor (dry matter=7%) and ten parts of tapwater plus 0.5 g/l of $(NH_4)_2HPO_4$. This suspension is used as the inoculum for preculture, by a shaking machine, in 1 l flasks with 200 ml of nutrient solution of the above composition (sterilization for 20 minutes at 121° C.). After an incubation time of 7 hours at 30° C., 20 l of nutrient solution of the above composition in 30 l small fermenters are inoculated with 2 flasks (0.4 l) and fermentation is carried out at 30° C. with 20 l of air per minute and a stirrer speed of 350 revolutions per minute. Shortly before the end of the logarithmic phase, after 8 hours, the culture is cooled and digested. For this, the 20 l of fermentation broth (14.4 units/ml of sucrose-mutase activity) are first concentrated with the aid of the Pellicon system, Durapore filter (0.5 µm) (Millipore) by cross-flow microfiltration to about 3 l of cell suspension (93.7 units/ml).

3 l of salt solution 0.5M NaCl, 0.05M K phosphate, pH 7.0, and 1% of Tween 20, prewarmed to 30° C., are added to the 3 l of cell suspension through a sterile filter and the entire suspension is stirred in the fermenter for 16 hours at room temperature at 30 revolutions per minute. Thereafter, the entire suspension is diluted with 24 l of sterile-filtered, deionized water and pumped through the Pellicon system to remove the cells and cell debris. The filtrate (7.6 units/ml) is then pumped via a stock container to another Pellicon system, polysulfone membrane 10000 (Millipore) and concentrated to about 3 l. The fermenter is filled again to 30 l with sterile deionized water, the mixture is subjected to microfiltration and, after admixing to the stock container, the filtrate is concentrated again to 3 l via the Pellicon system, polysulfone membrane. Diafiltration is now carried out via the stock vessel with about 60 l of 1 mM K phosphate, pH 7.0, and the product is thereby diluted to 9 l of so-called conditioned crude enzyme extract (17.6 units/ml, 1.9 mg/ml of protein).

0.5 l thereof is immediately pumped to an AMF-100 SP cartouche with a flow rate of 2.0 l/hour. Less than 0.5 unit/ml of protein, but still 1.9 mg/ml of protein, are to be measured in the eluate, that is to say the sucrose-mutase is almost selectively bonded from the crude enzyme extract onto the crosslinked, sulfonic acid web of the AMF cartouche.

Sterile-filtered 50% strength sucrose solution is now pumped through the AMF cartouche at room temperature and at a flow rate of 65 ml/hour. About 10–12% of sucrose (% content of the total sugar) are still detectable in the eluate, and the conversion is thus 88–90%. After 3 days of continuous operation, the bioreactor is brought continuously first to 25° C. and then to 30° C. At 25° C. and, respectively, 30° C., the conversion rises greatly and the throughput rate of the 50% strength sucrose solution is therefore increased to 120–140 ml/hour. The sucrose conversion thereby varies between 65% and 75%.

This long-term experiment is presented in FIG. 3 and shows that the sucrose-mutase can be employed in a highly purified form under these operating conditions for about one month, while retaining its activity, in the radial type bioreactor described above for the biotransformation of sucrose to isomaltulose.

A further 2 l of the crude enzyme extract (17.6 units/ml) stored under cool conditions in the stock vessel are now pumped over the above bioreactor. Only 1.4 units/ml were to be measured in the eluate, and thus about a further 32,000 units were bonded to the sulphonic acid AMF cartouche. The following eluate composition resulted with 50% strength sucrose solution and at a flow rate of about 210–220 ml/hour: 85.5% of isomaltulose, 11.0% of 1,1'-disaccharide, 2.5% of frustose and 1.0% of glucose; no sucrose was detectable.

The remaining 6.5 l of crude enzyme extract were now pumped from the stock vessel over the bioreactor. About 1.2 units/ml were not bonded, and the bioreactor was thus laden with a further 110,000 units.

The bioreactor was operated continuously for 5 days at a flow rate of 610 ml/hour and the following product spectrum was measured: 85.2% of isomaltulose, 10.2% of 1,1'-disaccharide, 2.1% of fructose and 0.8% of glucose.

When the flow rate was increased to 700 ml/hour, 3.2% of residual sucrose, 83.7% of isomaltulose, 10.2% of 1,1'-disaccharide, 2.1% of fructose and 0.6% of glucose resulted.

At a conversion of 97%, this means a constant throughput of about 7 reactor volumes of 50% strength sucrose solution per hour.

To determine the loading capacity of the bioreactor, 20 l of culture solution inoculated with *Protaminobacter rubrum* were again fermented (15.6 units/ml), and 9 l of crude enzyme extract (22.1 units/ml) were prepared under the same conditions and passed in portions over the bioreactor with a flow rate of about 1.32 l/hour.
Portion 1: 2 l, 1.9 units/ml in the eluate, 40,400 units thus bonded,
Portion 2: 2 l, 1.5 units/ml in the eluate, 41,200 units thus bonded,
Portion 3: 5 l, 1.5 units/ml in the eluate, 103,000 units this bonded.

Taking as a basis the 450 units/mg, quoted in DE-OS (German Published Specification) No. 3,038,218, of sucrose-mutase which is virtually electrophoretically pure, this means that about 335,000 units correspond to about 0.75 g of pure sucrose-mutase and could be bonded selectively from the crude enzyme extract to the sulfonic acid AMF web matrix in the 100 ml bioreactor.

EXAMPLE 2

Cells from a subculture of the strain *Serratia plymuthica* (ATCC 15928) are suspended in 10 ml of a thick liquor solution (5% dry matter content, 0.5 g/l of added $(NH_4)_2HPO_4$). This suspension is used as the inoculum for a preculture, on a shaking machine, in a 1 l flask with 200 ml of sterile nutrient solution of appropriate composition. After an incubation time of 15 hours at 30° C., 18 l of nutrient solution of the above composition are inoculated with in each case 10 flasks (2 l) in a 30 l small fermenter and fermentation is carried out at 30° C. with 20 l of air/minute at a stirrer speed of 350 revolutions per minute. Shortly before the end of the logarithmic phase, after 10 hours, the culture is cooled.

The process steps of cell digestion, cross-flow microfiltration and dialfiltration were carried out analogously to Example 1. The concentration of NaCl in the salt solution, however, was 1 molar.

Data for the individual process steps: 20 l of fermentation broth of 7.1 units/ml, 3 l of concentrate of 44.7 units/ml, 30 l of microfiltrate of 3.9 units/ml, 10 l of retained material from the dialfiltration of 10.8 units/ml (crude enzyme extract).

1 l of the retained material from the diafiltration (1 mM K phosphate, pH 7.0) were pumped onto an AMF-100 SP cartouche, flow rate 1.2 l/hour. A sucrose-mutase activity of 0.45 unit/ml was measured in the eluate. At a continuous throughput of 50% strength sucrose solution (sterile-filtered), a conversion of 94.5% of sucrose was to be measured at a throughput rate of 90 ml/hour at 30° C. The other 9 l of the crude enzyme extract were also pumped over the bioreactor at a flow rate of 1.2 l/hour. The eluate had 0.4 unit/ml of sucrose-mutase.

EXAMPLE 3

Cells from a subculture of the strain *Erwinia carotovora* (ATCC 25206) are suspended in 10 ml of a thick liquor solution (5% dry matter content, 0.5 g/l of added $(NH_4)_2HPO_4$). This suspension is used as the inoculum for a preculture, on a shaking machine, in a 1 l flask with 200 ml of nutrient solution of appropriate composition. After an incubation time of 30 hours at 30° C., 18 l of nutrient solution of the above composition are inoculated with in each case 10 flasks (2 l) in a 30 l small fermenter and fermentation is carried out at 30° C. with 20 l of air/minute at a stirrer speed of 350 revolutions per minute. Shortly before the end of the logarithmic phase, after 18 hours, the culture is cooled and digested.

The retained material, obtained analogously to Example 2, from the diafiltration, a crude enzyme extract with an activity of 3.9 units/ml (fermentation solution of 5.6 units/ml) in a total volume of 10 l, was pumped over an AMF-100 SP cartouche at a flow rate of 1.2 l/hour. The eluate contained 0.15 unit/ml of sucrose-mutase. On subsequent continuous throughput of sterile-filtered 50% strength sucrose solution, 190 ml/hour, 30° C., only 2% of residual sucrose (% content in the total sugar) was measured.

The term "conditioned crude enzyme extract" is to be understood as meaning cell-free culture supernatant, or corresponding diafiltrate, which contains sucrose-mutase and has been adjusted to the parameters, for example salt concentration, conductivity and pH value, for selective bonding to an anionisable carrier matrix.

Figure 2A:
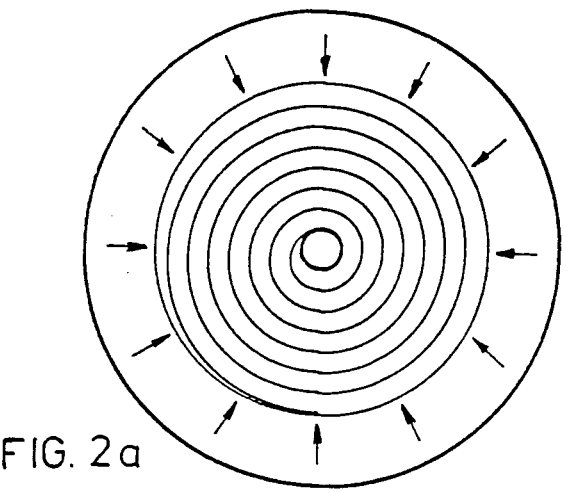
Figure 2B:
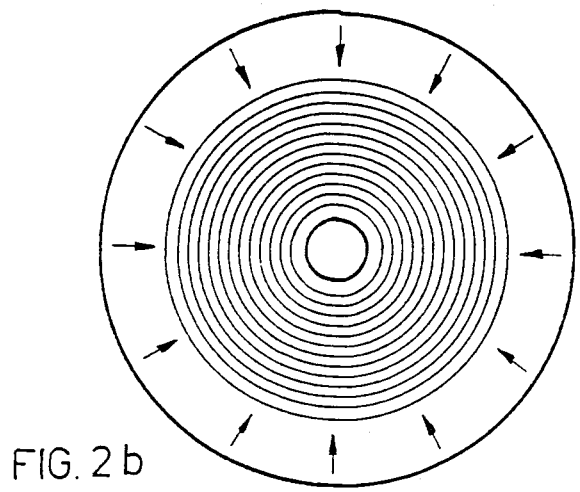
Figure 3:
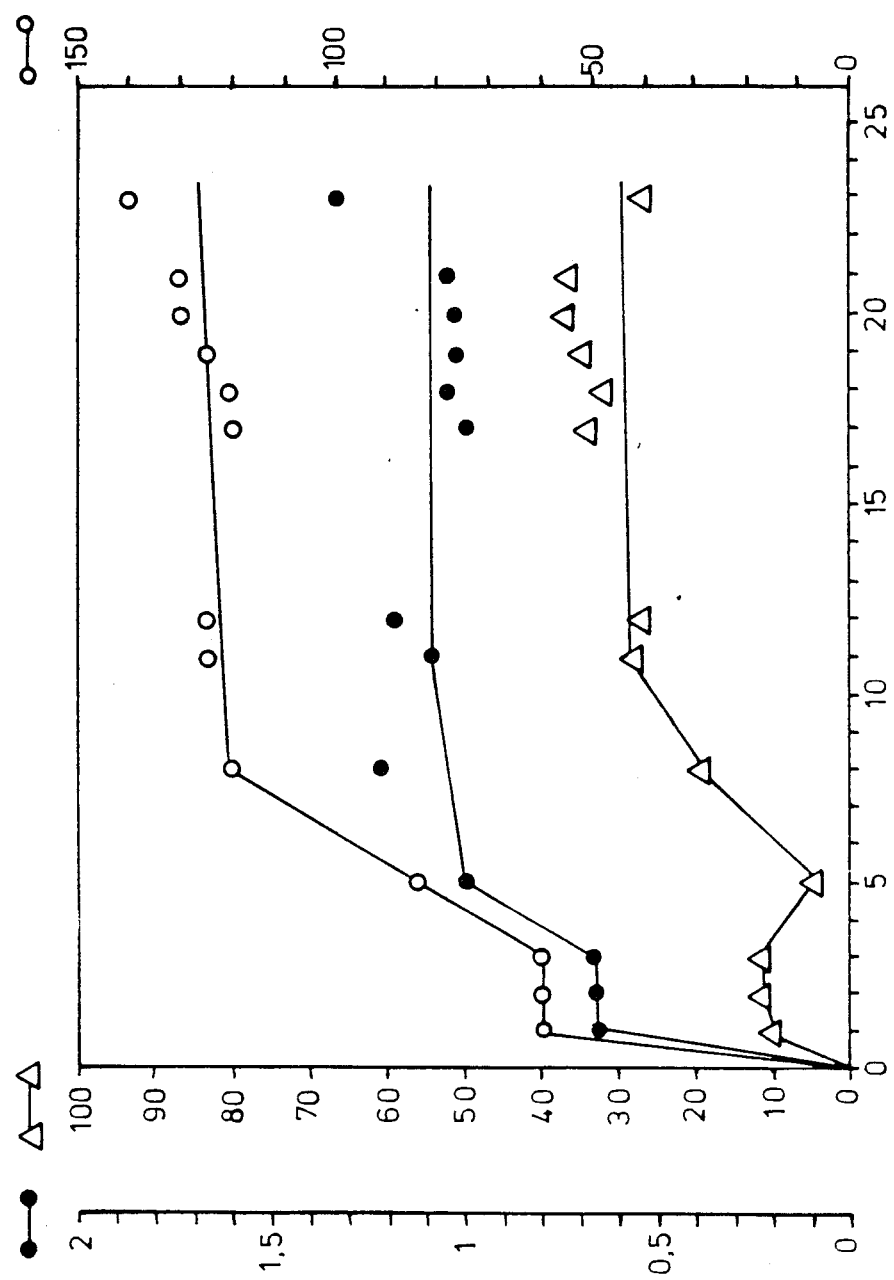

The term "radial type bioreactor" is explained in the Application text in connection with FIGS. 2a and 2b.

Figure 1A:
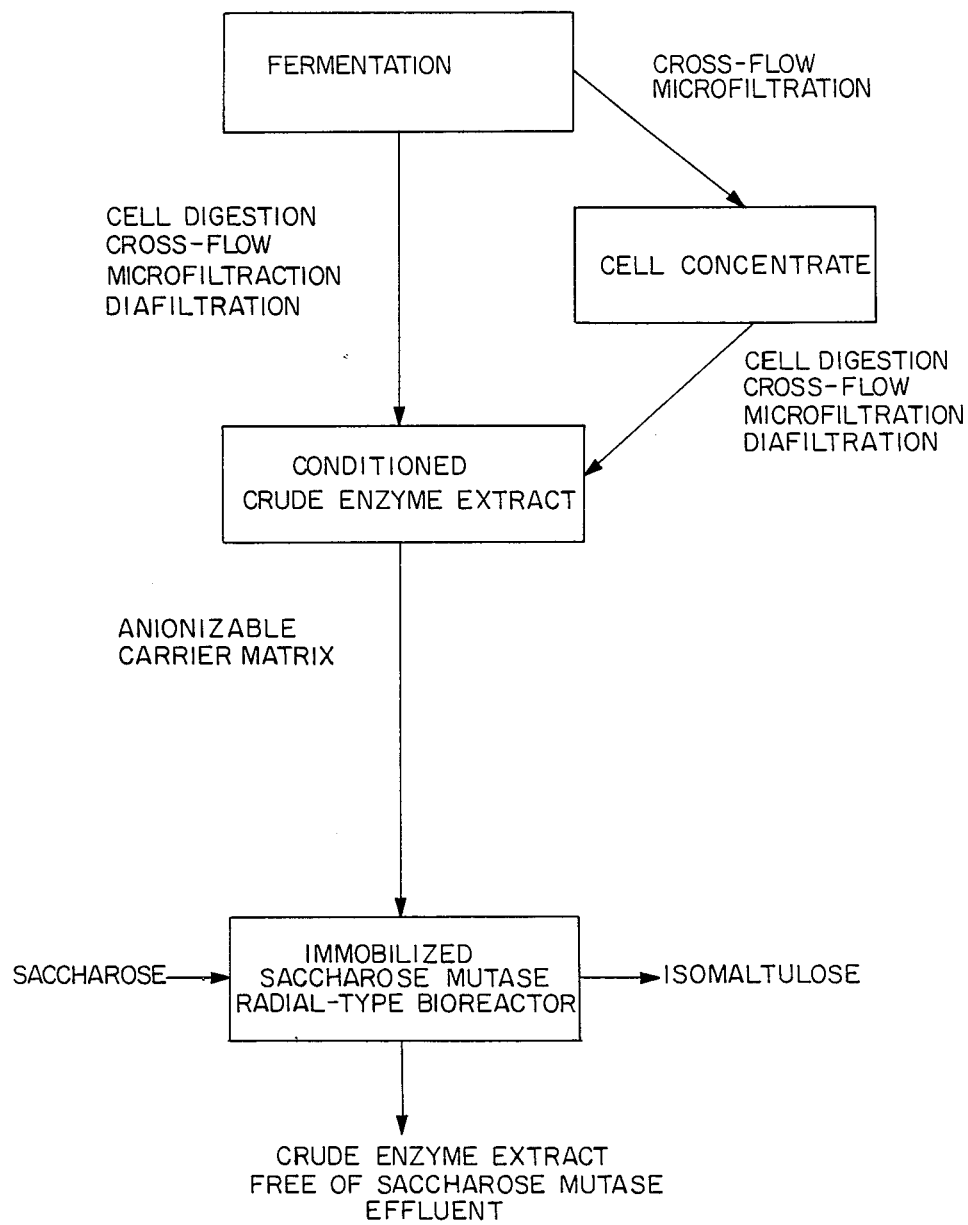
FIG. 1a:
Flow charts of the process according to the invention.
Figure 1B:
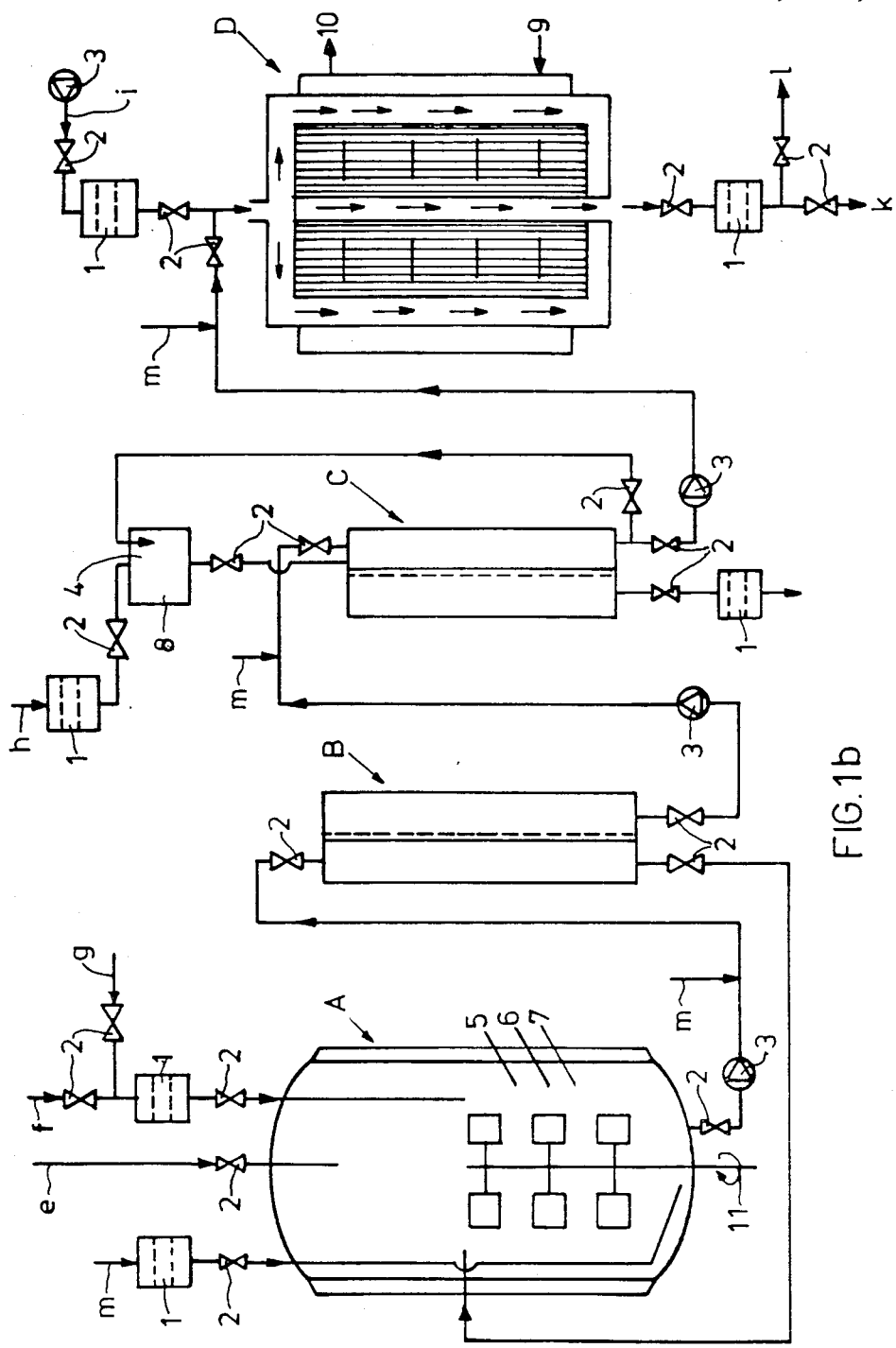

FIG. 1b:
Reactor unit for continuous enzymatic preparation of isomaltulose (not to scale).

The unit consists of 4 reactor sub-units.
(A) the fermenter
(B) the unit for cross-flow microfiltration
(C) the unit for diafiltration (D) the radial type bioreactor.

The process steps a–d according to the invention (according to the text) are divided amongst the unit as follows: (a) and (b) are carried out in the fermenter (A), (b) is carried out in unit (B), and (c) and (d) are carried out in the radial type bioreactor (D). The diafiltration unit is used for conditioning of the crude enzyme extract.

Other details of the unit are:
(1) sterile filter/filter candles
(2) control, shut-off valves
(3) pump with indication of the delivery direction
(4) stock containers for the diafiltration
(5), (6), (7) measurement probes on the fermenter, for example pressure, temperature, gas sampling, liquid
(8) sample probe on the stock vessel
(9), (10) thermostat feed and discharge on the radial type bioreactor
(11) stirrer with sterile aeration on the fermenter.

Other process steps on the reactor unit are:
(e) addition of nutrient solution via continuous sterilization, inoculum
(f) addition of salt solution, for example NaCl or KCl
(g) addition of surface-active reagents
(h) addition of conditioning solution, for example 1 mM potassium phosphate, pH 7.0
(i) throughput of sucrose solution through the radial type bioreactor and
(k) removal of the product stream for crystallisation of the isomaltulose
(l) discharge of the sucrose-mutase-free crude enzyme extract after loading of the radial type bioreactor
(m) sterilisation of the part unit with steam.

FIGS. 2a and b

Cross-section through the radial type bioreactor.

The membrane-like carrier or web matrix selectively laden with the enzyme is either wound up cylindrically (2a) or used in the form of concentrically arranged cylindrical sheets (2b). The wound form (2a) is an approximation of the concentric ideal form which is easier to produce. In both cases, the material stream, however, passes through the web layers from the outside radially towards the inside to the cylinder axis. The wound form is a good approximation of the concentric form, especially as the flow rate increases.

FIG. 3

Sucrose-mutase radial type bioreactor:

Throughput and conversion of surcose and stability of the carrier-bonded enzyme (compare Example 1).
Ordinates:
Δ—Δ: residual sucrose in %
o—o: flow rate in ml/hour
o—o: isomaltulose in kg/day.
The time in days is given on the abscissae.
What is claimed is:

1. A continuous process for the enzymatic preparation of isomaltulose which can be operated under sterile conditions comprising
   (a) preparing sucrose-mutase by fermentation of microorganisms which form sucrose-mutase, treating the cells with salt solution and surface-active reagents before the end of the logarithmic growth phase,
   (b) preparing a cell-free crude enzyme extract by cell digestion and cross-flow microfiltration,
   (c) simultaneously purifying and immobliizing the sucrosemutase from this crude extract by selective bonding to a sulfonic acid cation exchanger matrix and
   (d) bringing the matrix thereby obtained into contact with sucrose.

2. A process according to claim 1, wherein process step (c) is carried out in the pH range of 4–12 at salt concentrations of less than 0.2M.

3. A process according to claim 1, wherein process step (b) is carried out by treatment of the fermentation solution in the pH range of 4–12 at salt concentrations of 0.1M to 3.0M.

4. A process according to claim 3, wherein process step (b) is carried out in the presence of a surface-active reagent in the concentration range of 0.1–5.0% (weight/volume).

5. A process according to claim 1, wherein a cellulose web in cartridge or cartouche form which is crosslinked by bifunctional polymers and has functional sulfonic acid groups bonded via vinyl polymers is used as the sulfonic acid cation exchanger matrix, the carrier material being wound in cylindrical shape, with or without spaces between the layers of cellulose web, and being such that the matter can flow through radially from the outside inwards.

6. A process according to claim 1, wherein the enzyme sucrose-mutase is produced by fermentation of *Protaminobacter rubrum* in process step (a).

7. A process according to claim 1, wherein the enzyme sucrose-mutase is produced by a fermentation of *Serratia plymuthica* in process step (a).

8. A process according to claim 1, wherein the enzyme sucrose-mutase is produced by fermentation of a microorganism of the genus Erwinia in process of step (a).

9. A process according to claim 1, wherein process step (d) is carried out in the pH range 4–8 with a surcrose solution of concentration of 10–70% in the temperature range of 10°–40° C.

10. A process according to claim 2 wherein process step (c) is carried out at a salt concentration of 1 μM to 10 μM.

11. A process according to claim 3 wherein process step (b) is carried out in the presence of an alkali metal chloride.

12. A process according to claim 9 wherein process step (d) is carried out in the pH range of 4.7–7.5, a sucrose solution of concentration 30–60%, in the temperature range of 25°–35° C.

13. A process according to claim 1, wherein a radial type reactor is used for the enzyme immobilization and the biotransformation is carried out in the thus prepared radial type bioreactor.

* * * * *